United States Patent
Niemeyer

(10) Patent No.: US 10,342,464 B2
(45) Date of Patent: Jul. 9, 2019

(54) 3D CAMERA SYSTEM FOR INFANT MONITORING

(71) Applicant: Intel Corporation, Santa Clara, CA (US)

(72) Inventor: Erik A. Niemeyer, Rio Rancho, NM (US)

(73) Assignee: Intel Corporation, Santa Clara, CA (US)

(*) Notice: Subject to any disclaimer, the term of this patent is extended or adjusted under 35 U.S.C. 154(b) by 802 days.

(21) Appl. No.: 14/837,169

(22) Filed: Aug. 27, 2015

(65) Prior Publication Data

US 2017/0055877 A1    Mar. 2, 2017

(51) Int. Cl.
*A61B 5/113* (2006.01)
*A61B 5/00* (2006.01)
*A61B 5/08* (2006.01)

(52) U.S. Cl.
CPC ............ *A61B 5/113* (2013.01); *A61B 5/0077* (2013.01); *A61B 5/0826* (2013.01); *A61B 5/0022* (2013.01); *A61B 5/746* (2013.01); *A61B 2503/04* (2013.01)

(58) Field of Classification Search
CPC ..... A61B 5/113; A61B 5/0826; A61B 5/0077; A61B 5/0022; A61B 5/746; A61B 2503/04

USPC ......................................................... 382/128
See application file for complete search history.

(56) References Cited

U.S. PATENT DOCUMENTS

| | | | |
|---|---|---|---|
| 2011/0060215 A1* | 3/2011 | Tupin, Jr. ............. | A61B 5/0507 600/425 |
| 2013/0321571 A1* | 12/2013 | Vandewalle ......... | H04N 13/106 348/42 |
| 2015/0105670 A1* | 4/2015 | Bresch ................ | A61B 5/0077 600/479 |
| 2015/0265187 A1* | 9/2015 | Bernal ................ | A61B 5/1128 600/474 |

* cited by examiner

*Primary Examiner* — Amandeep Saini
(74) *Attorney, Agent, or Firm* — Green, Howard, & Mughal LLP.

(57) ABSTRACT

Systems and methods employing a depth-sensing camera to detect abdomen rise and fall during an infant sleep period, or lack thereof due to respiratory arrest. Visual processing of image data collected by one or more 3D digital camera is performed to detect the infant and to measure a distance between an infant's abdominal cavity and a camera baseline over time. An alarm may be triggered at by the system, locally and/or at remote devices, such as a mobile phone, tablet, laptop, etc. The monitoring system may also detect situations when an infant rolls from a back-sleeping to a belly-sleeping position.

17 Claims, 8 Drawing Sheets

3D CAMERA SYSTEM FOR INFANT MONITORING

BACKGROUND

Sudden infant death syndrome (SIDS), also known as crib death, is the sudden unexplained death of a child less than one year of age. SIDS usually occurs during sleep and is currently believed to be associated with respiratory issues. Typically, infant death occurs between the hours of 00:00 and 09:00 with no noise detected. SIDS was the third leading cause of death in children less than one year old in the United States in 2011. About 90% of cases happen before six months of age, with it being most frequent between two months and four months of age.

Conventional approaches to detecting an infant respiratory problem in real time require physical attachment of devices to the infant, or have difficult coping with background noise within the infant's environment. A more robust system for infant respiratory monitoring is therefore needed.

Digital cameras are often included in infant monitoring systems, for example installed in a nursery. Such systems typically relay video data, or audio/video (A/V) data, from the camera to a remote display screen. Allowing a caregiver to visualize the infant, for example during a daytime napping period. Such systems are however relatively unsophisticated, lacking significant image analysis capability.

BRIEF DESCRIPTION OF THE DRAWINGS

The material described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. In the figures.

DETAILED DESCRIPTION OF EXEMPLARY EMBODIMENTS

Figure 1:
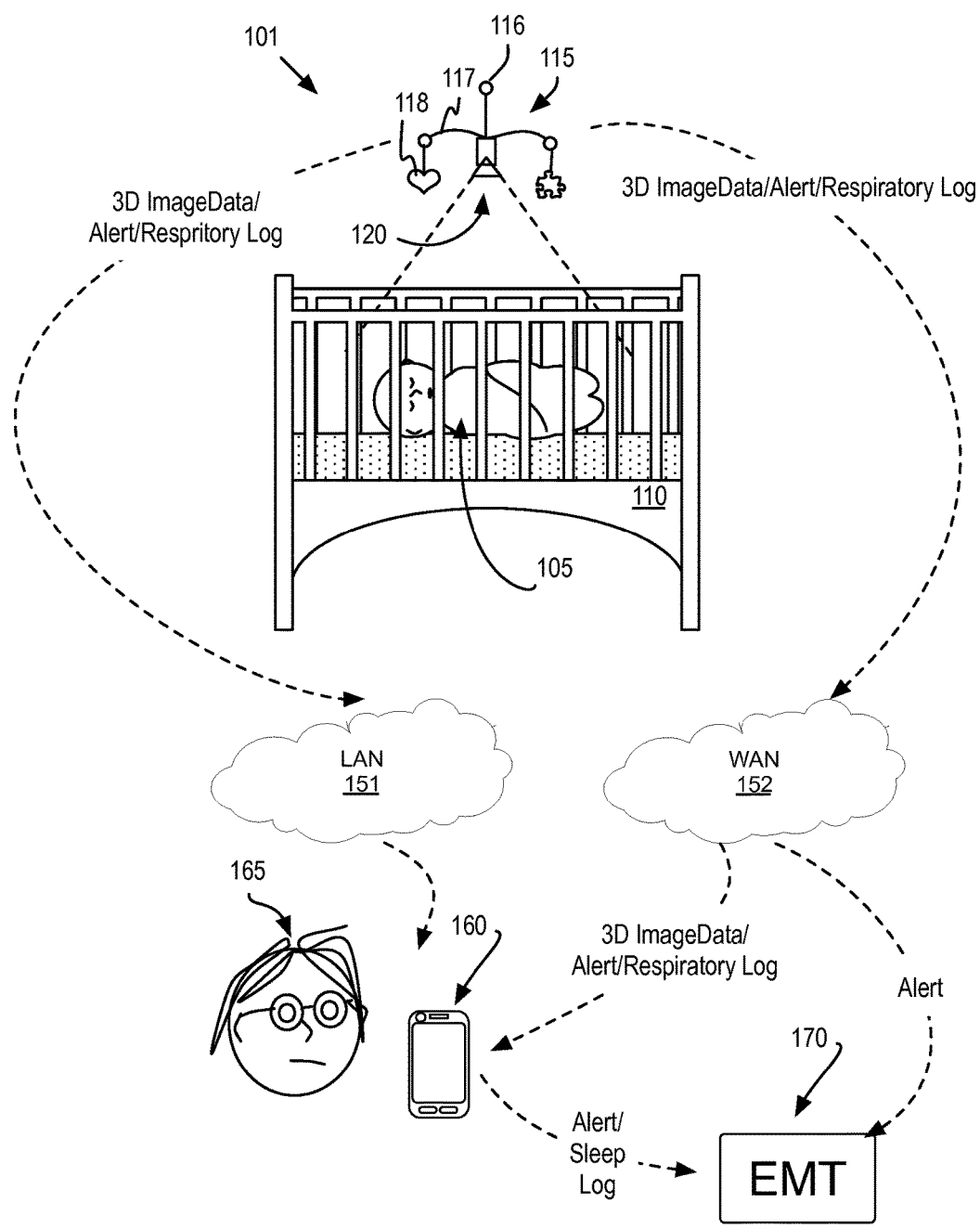
FIG. 1 is a schematic of a 3D camera system for infant monitoring, in accordance with some embodiments.

One or more embodiments are described with reference to the enclosed figures. While specific configurations and arrangements are depicted and discussed in detail, it should be understood that this is done for illustrative purposes only. Persons skilled in the relevant art will recognize that other configurations and arrangements are possible without departing from the spirit and scope of the description. It will be apparent to those skilled in the relevant art that techniques and/or arrangements described herein may be employed in a variety of other systems and applications beyond what is described in detail herein.

Reference is made in the following detailed description to the accompanying drawings, which form a part hereof and illustrate exemplary embodiments. Further, it is to be understood that other embodiments may be utilized and structural and/or logical changes may be made without departing from the scope of claimed subject matter. Therefore, the following detailed description is not to be taken in a limiting sense and the scope of claimed subject matter is defined solely by the appended claims and their equivalents.

In the following description, numerous details are set forth, however, it will be apparent to one skilled in the art, that embodiments may be practiced without these specific details. Well-known methods and devices are shown in block diagram form, rather than in detail, to avoid obscuring more significant aspects. References throughout this specification to "an embodiment" or "one embodiment" mean that a particular feature, structure, function, or characteristic described in connection with the embodiment is included in at least one embodiment. Thus, the appearances of the phrase "in an embodiment" or "in one embodiment" in various places throughout this specification are not necessarily referring to the same embodiment. Furthermore, the particular features, structures, functions, or characteristics described in the context of an embodiment may be combined in any suitable manner in one or more embodiments. For example, a first embodiment may be combined with a second embodiment anywhere the particular features, structures, functions, or characteristics associated with the two embodiments are not mutually exclusive.

As used in the description of the exemplary embodiments and in the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items.

As used throughout the description, and in the claims, a list of items joined by the term "at least one of" or "one or more of" can mean any combination of the listed terms. For example, the phrase "at least one of A, B or C" can mean A; B; C; A and B; A and C; B and C; or A, B and C.

The terms "coupled" and "connected," along with their derivatives, may be used herein to describe functional or structural relationships between components. It should be understood that these terms are not intended as synonyms for each other. Rather, in particular embodiments, "connected" may be used to indicate that two or more elements are in direct physical, optical, or electrical contact with each other. "Coupled" may be used to indicated that two or more elements are in either direct or indirect (with other intervening elements between them) physical, optical, or electrical contact with each other, and/or that the two or more elements co-operate or interact with each other (e.g., as in a cause an effect relationship).

Some portions of the detailed descriptions provide herein are presented in terms of algorithms and symbolic representations of operations on data bits within a computer memory. Unless specifically stated otherwise, as apparent from the following discussion, it is appreciated that throughout the description, discussions utilizing terms such as "calculating," "computing," "determining" "estimating" "storing" "collecting" "displaying," "receiving," "consolidating," "generating," "updating," or the like, refer to the action and processes of a computer system, or similar electronic computing device, that manipulates and transforms data represented as physical (electronic) quantities within the computer system's circuitry including registers and memories into other data similarly represented as physical quantities within the computer system memories or registers or other such information storage, transmission or display devices.

While the following description sets forth embodiments that may be manifested in architectures, such system-on-a-chip (SoC) architectures for example, implementation of the techniques and/or arrangements described herein are not restricted to particular architectures and/or computing systems, and may be implemented by any architecture and/or computing system for similar purposes. Various architectures employing, for example, multiple integrated circuit (IC) chips and/or packages, and/or various computing devices and/or consumer electronic (CE) devices such as set-top boxes, smartphones, etc., may implement the techniques and/or arrangements described herein. Further, while the following description may set forth numerous specific details such as logic implementations, types and interrelationships of system components, logic partitioning/integration choices, etc., claimed subject matter may be practiced without such specific details. Furthermore, some material such as, for example, control structures and full software instruction sequences, may not be shown in detail in order not to obscure the material disclosed herein.

Certain portions of the material disclosed herein may be implemented in hardware, for example as logic circuitry in an image processor. Certain other portions may be implemented in hardware, firmware, software, or any combination thereof. At least some of the material disclosed herein may also be implemented as instructions stored on a machine-readable medium, which may be read and executed by one or more processors (graphics processors and/or central processors). A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical, or other similarly non-transitory, tangible media.

One or more system, apparatus, method, and computer readable media is described below for respiratory monitoring based on collection and processing of 3D image data. In some embodiments, abdominal cavity movement is assessed based on depth maps determined for each of a plurality of image frames collected over a time interval.

In some embodiments, an infant sleep period is monitored by a respiratory monitor mounted over a crib with a field of view of a 3D camera including the entire crib mattress. In some embodiments, object detection algorithms, such as, but not limited to, facial recognition algorithms, are employed to detect the infant. In further embodiments, a failure in facial recognition triggers an alert that the infant may have rolled to a belly-sleeping position, or the infant's face is otherwise occluded. A region of interest (ROI) within the image frame may be selected, for example an abdominal cavity region determined based on the position of a detected object. In some embodiments, a depth map is determined for each of a plurality of image frames within at least the ROI. The depth map may be stored in associated with a timestamp and depth values analyzed as a function of time to determine abdominal cavity movement as a technique for monitoring respiration.

In some embodiments, a respiratory cycle is determined based on the depth values stored as a function of time. In further embodiments, the respiratory cycle is assessed relative to one or more respiratory cycle metrics. In some exemplary embodiments, an alert is triggered if either frequency or depth (i.e., magnitude) of the respiratory cycle fails to satisfy one or more predetermined thresholds.

FIG. 1 is a schematic of a 3D camera-based infant monitoring system 101, in accordance with some embodiments. System 101 includes a 3D camera platform 120, which is configured to output at least one of 3D image data, collected respiratory data (e.g., a time log of respiration), or one or more alert. 3D camera platform 120 is positioned within system 101, ideally so that a geometry of the world scene is known with respect to the camera. In the exemplary embodiment, 3D camera platform 120 is integrated into a nursery fixture, such as a mobile 115. Mobile 115 includes a mount 116, for example to attached to a room ceiling over crib 110, or to crib 110, and one or more arms 117 from which sensory objects 118 are suspended. In this exemplary embodiment, 3D camera platform 120 is mounted to have image sensors collecting image data of a world scene encompassing the entire interior of crib 110. 3D camera platform 120 is positioned above the infant subject. During operation, system 101 collects image data for a camera field of view including infant subject 105. While mobile integration may provide an advantageous viewpoint where the depth dimension is perpendicular to the planar surface of a mattress in crib 110. 3D camera platform 120 may be alternatively mounted directly to crib 110, or other furniture or ceiling fixture (not depicted). 3D camera platform 120 may include one or more camera module mounted in any manner known to be suitable for a home security camera. For example, single camera platforms may be mounted in two or more corners of a room in which crib 110 is disposed.

3D camera platform 120 includes one or more digital cameras operable to collect information from which depth (i.e., range) information may be determined for an image frame. Any cameras known to be capable of generating 3D image frame data may be employed. In some embodiments, 3D camera platform 120 includes at least one of: a stereo camera or other array camera, time-of-flight (TOF) camera, or structured light camera system.

In some stereo camera embodiments, 3D camera platform 120 is a mobile computing device including a plurality of camera hardware modules (CM) with a predetermined baseline relationship. In some exemplary embodiments, three camera hardware modules are included. However, any number of camera hardware modules and/or image sensors may be included in an array camera. Each of the plurality of camera modules associated with 3D camera platform 120 may collect an input image captured from a different camera viewpoint. In exemplary embodiments, images captured from the different viewpoints are captured at substantially the same instant of time such that they contain image data for a given scene. One of the three image frames may be designated as a reference and combined into an image frame having depth or range (z) information, or disparity information indicative of depth for each 2D (x,y) spatial position within the image frame. For example, where one of the CM has a higher resolution (e.g., 8 megapixel, or more) than the other camera modules (e.g., 720p, HD, etc.), the high resolution CM may provide a default reference RGB/IR image. The lower resolution cameras may be considered supplemental to the reference and are each associated with predetermined baseline vector (length and direction) from the higher resolution CM to generate depth data (D). The 3D image output from 3D camera platform 120 may then be associated with RGB/IR-D data for each 2D spatial position with the input image frame.

In an exemplary embodiment where 3D camera platform 120 is integrated into mobile 115, the baseline vector between the reference camera module and each supplemental camera module may have a length of tens of millimeters to tens of centimeters, depending on the form factor. In one exemplary embodiment 3D camera platform 120 includes two lower resolution CM modules disposed on opposite sides of one higher resolution CM spaced by known distances from the higher resolution CM. Distances between 3D camera platform 120 and a mattress within crib 110 may be 1-3 meters for example. In other embodiments, where 3D camera platform 120 employs more than one separate infrastructure camera fixtures, baseline lengths may be on the order of meters.

In some embodiments, 3D camera platform 120 performs image processing according to one or more respiratory monitoring algorithm and streams out a respiratory log in substantially real time to one or more remote location during operation of system 101. In some embodiments, 3D camera platform 120 streams 3D image data in substantially real time to one or more remote location. For such embodiments, 3D camera platform 120 may also perform image processing according to one or more respiratory monitoring algorithm in substantially real time, or not. In some embodiments, 3D camera platform 120 triggers an auditory and/or visible alert (e.g., siren, alarm, etc.) according to one or more respiratory or other monitoring algorithm. The alert may be local to crib 110, or transmitted to a remote device through a wired and/or wireless network. In some embodiments, one or more of 3D image data, logged respiratory data, or alerts is communicated by 3D camera platform 120 over a local area network 151 to a mobile computing platform 160 (e.g., smart phone, tablet computer, etc.) associated with a caregiver, or system user 165. In some embodiments, one or more of 3D image data, logged respiratory data, or alerts is communicated by 3D camera platform 120 over a wide area network 152 to mobile computing platform 160 (e.g., smart phone, tablet computer, etc.) associated with system user 165. In some embodiments, one or more of 3D image data, logged respiratory data, or alerts is communicated by 3D camera platform 120 over wide area network 152 to a system user 165 and/or an emergency responder 170, such as an emergency medical technician.

3D camera platform 120 may encode image frames where a wireless or wired data channel has insufficient bandwidth to timely send the frame data in an uncompressed format. Depending on the available channel bit rate, a given frame may be compressed to provide a higher or lower quality representation. In some embodiments, 3D camera platform 120 complies with one or more wireless display specifications (e.g., WiDi v3.5 by Intel Corporation, and Wi-Fi Display v1.0 or WFD from the Miracast program of the Wi-Fi Alliance) have been developed for the transmission of compressed graphics/video data and audio data streams over wireless local area networks. For example, current wireless display technologies utilizing WiFi technology (e.g., 2.4 GHz and 5 GHz radio bands) are capable of streaming encoded full HD video data as well as high fidelity audio data (e.g., 5.1 surround).

Figure 2:
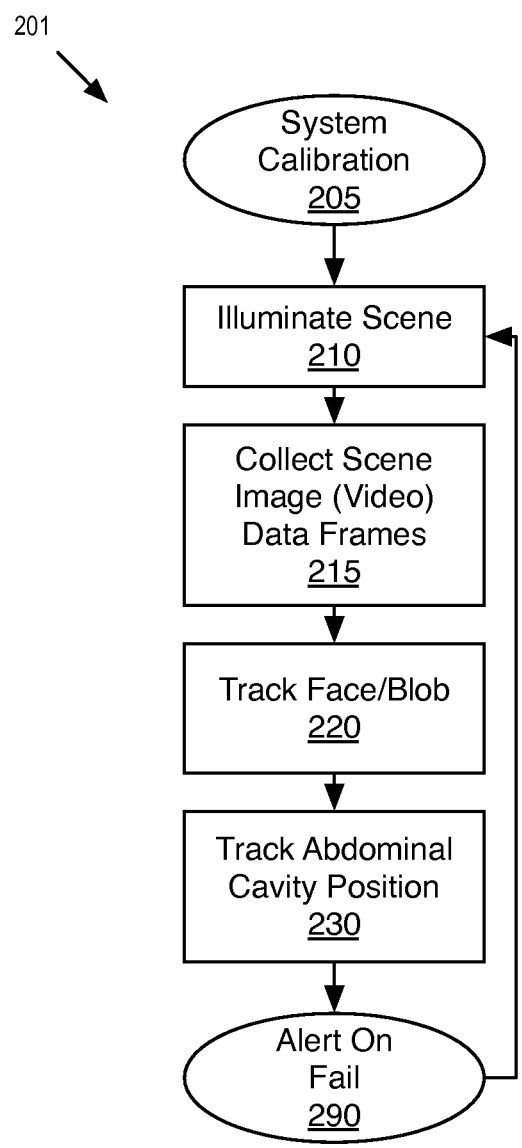
FIG. 2 is a flow diagram of a method for infant monitoring with a 3D camera system, in accordance with some embodiments.

FIG. 2 is a flow diagram of a method 201 for infant monitoring with a 3D camera system, in accordance with some embodiments. In some embodiments, method 201 is performed by monitoring system 101 (FIG. 1). In exemplary embodiments, method 201 is performed by computer processor(s) integrated into 3D camera platform 120. In other embodiments, at least a portion of method 201 is performed by a computer processor remote from 3D camera platform 120.

Method 201 begins with system calibration at operation 205. Calibration operation 205 may be divided between environment-specific calibration and subject-specific calibration. Calibration operation 205 may also be dependent on the 3D camera platform employed to implemented method 201. TOF, structured light, and stereo camera platforms each have known calibration techniques for determining world scene geometry, and any of them may be employed at operation 205 to determine the geometry of the field of view with respect to the camera baseline. Initial auto-calibration routines may be performed to arrive at accurately measured real-world range (i.e., distance, or depth) between the 3D camera platform baseline and a reference surface, such as that of a crib mattress.

Following the environmental calibration, accurate depth data is generated by platform 120. Subject-specific calibration routines may then be performed at operation 205 for one or more of: teaching object detection algorithms (e.g., facial recognition), and building a respiratory cycle baseline from which one or more respiratory metrics may be determined specific to the infant subject to be monitored. In some embodiments, operation 205 is conducted during a controlled or "known good" sleeping period for the infant subject. In some exemplary embodiments, operation 205 further entails performing operations 210, 215, 220, and 230 (described further below) during the baseline sleeping period. Performance of these operations may then be distinguished between the calibration phase, during which the system is generating baseline respiratory data, and a runtime, during which the system will issue event-based alerts at operation 290. Respiratory metrics determined during the calibration phase may be employed as the basis for triggering alerts during the runtime.

At operation 210, the scene is illuminated. While scene illumination may be within the visible (RGB) band, exemplary embodiments illuminate the scene over the near infra red (NIR) band. Such embodiments advantageously enable low light 3D image data collection, for example during nighttime infant sleeping periods. In some embodiments, scene illumination at operation 210 is limited to the NIR. As used herein, the RGB band extends between 400 nm up to 700 nm, while the NIR band extends from about 701 nm to at least 1200 nm. For NIR illumination embodiments, at least one camera platform includes one or more NIR light emitting diode (LED) and an RGBNIR camera sensor, which may be any known CMOS sensor without a hot mirror in the optical path, or an enhanced NIR sensor including a specific NIR sensitive pixels.

Method 201 continues at operation 215, where scene information is collected in the form of consecutive image data frames (i.e., video frames). In exemplary embodiments, the scene information collected at operation 215 is through a lens having a field of view encompassing an entire area of a crib mattress within a crib at the working distance (e.g., 1-3 m). In exemplary embodiments, the scene information collected at operation 215 includes an infant subject. The image data frames collected at operation 215 comprises 3D image data including depth information, in addition to color information (e.g., intensity for each of a plurality of color channels in any color space, such as RGB, YPbPr, YCbCr, or the like). In some embodiments, depth information collected at operation 215 is in the form of a depth map correlated with a plurality of pixels $p_i$, each having an image coordinate $x_i, y_i$ associated with the input image frame. In other embodiments, the depth information collected at operation 215 is in the form of a disparity map correlated with the plurality of pixels $p_i$, each having an image coordinate $x_i, y_i$ associated with the input image. A disparity value associated with a pixel indicates the correspondence of the pixel in one image (e.g., collected by a first camera module in the 3D camera platform) to a pixel in another image (e.g., collected by a second camera module in the 3D camera platform). The disparity estimation may be by any technique, as embodiments herein are not limited in this respect. There may be a depth or disparity value associated with each pixel of an image frame, or some depth/disparity values may be absent in the event of a camera occlusion and/or textureless surface, etc. For some embodiments, a 3D (X,Y,Z) spatial coordinate map is generated at operation 215. Any mapping functions may be utilized to determine 3D spatial coordinates from a disparity value at the corresponding pixel position, for example based on predetermined camera parameters.

In the exemplary embodiment illustrated in FIG. 2, an object within the image data frames is detected and tracked at operation 220. A real-time visual object detection and/or tracking algorithm may be employed to detect and track the infant subject across consecutive frames. One objective of tracking is to associate objects in consecutive images, based on the detection or tracking of previous image frames. Real-time visual object tracking may entail processing the video data stream at the camera frame-rate to determine automatically a bounding box of the infant subject, or determine that the object is not visible, in each frame. Infant movement is expected to be limited during a sleeping period, and so many challenges associated with real time object tracking are reduced in the exemplary embodiments. Adaptive tracking-by-detection methods are widely used in computer vision for tracking arbitrary objects, and any such technique may be employed at operation 220 to determine the location of the infant object in relation to the 3D camera platform.

In some embodiments, the object detected includes one or more facial feature. Embodiments may employ any known facial feature detection methods, such as, but not limited to, geometry and color-based techniques. Although eyes are often employed, for exemplary embodiments where monitoring during sleep periods is desired, facial recognition features exclude the eyes (e.g., are limited to nose, mouth, head). Other techniques, including blob detection, may be employed to detect and track infant shape, which is a relatively predictable form and is also expected to be relatively static over a sequence of images captured from a camera spanning an infant sleeping period. Thermal imaging data may also be collected by the 3D camera platform, and employed for tracking position of the subject infant.

Figure 3:
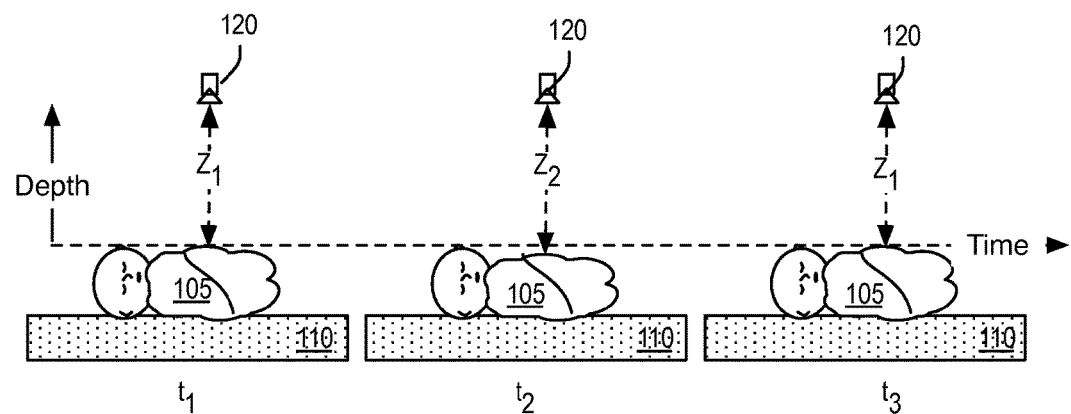
FIG. 3 is a schematic of infant abdominal cavity distance measurement with a 3D camera system, in accordance with some embodiments.

At operation 230, a relative position of an abdominal cavity of the infant subject is tracked over time. In other words, abdominal cavity movement relative to the 3D camera platform in a fixed position is tracked). In exemplary embodiments, abdominal cavity movement is tracked on the basis of depth information collected from a 3D camera platform. FIG. 3 is a schematic of infant abdominal cavity distance measurement with a 3D camera system, in accordance with some embodiments. As shown, over three points in time $t_1$, $t_2$, $t_3$ representing a full respiratory cycle, a distance between a baseline associated with 3D camera platform 120 and a surface associated with the abdominal cavity of infant 105 varies from $z_1$ at peak exhale, to $z_2$ at peak inhale, and back to $z_1$.

Noting that infants are predominantly belly breathers, the abdominal cavity of an infant may be expected to move by 3 mm, or more, during the respiratory cycle including exhalation and inhalation half cycles. Noting further that it is generally desirable for infants to sleep on their backs, for example to avoid potential respiratory problems, movement of the abdominal cavity is then primarily in a direction perpendicular to a mattress surface during the sleeping period. Movement of the abdominal cavity is then primarily in the depth dimension of a 3D camera platform advantageously positioned directly above the crib mattress as illustrated in FIG. 3. For 3D camera platforms positioned in locations other than directly above the crib mattress, greater depth resolution may be needed as a function of geometry. 3D camera platforms with at least 3 mm depth resolution are now commercially available (e.g., RealSense™ 3D camera from Intel Corporation).

Figure 4:
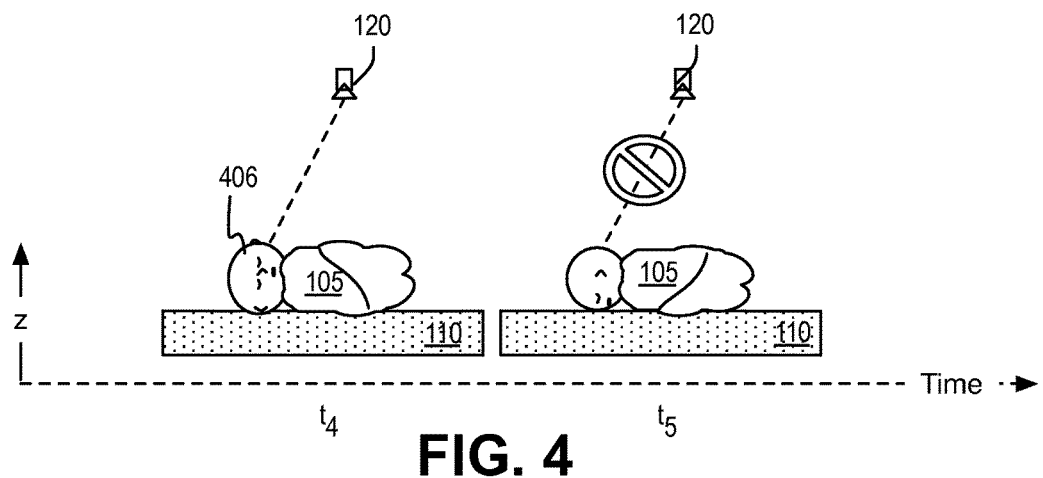
FIG. 4 is a schematic of infant roll detection with a 3D camera system, in accordance with some embodiments.

In some embodiments, abdominal cavity tracking at operation 230 is conditioned upon satisfaction of a back sleeping criteria. For example, abdominal cavity tracking operation 230 may be predicated upon successful object detection at operation 220. In some embodiments therefore, an infant roll alert may be issued at operation 290 in response to an object detection failure at operation 220. FIG. 4 is a schematic illustrating infant roll detection with a 3D camera system, in accordance with some embodiments. As shown, at a first point in time $t_4$, 3D camera platform 120 successfully detects infant facial features 406 for one or more image frames, and in response, depth information associated with these frames is processed during abdominal cavity tracking operation 230. At a later point in time $t_5$ (FIG. 4), 3D camera platform 120 fails to detect a facial features 406 for one or more image frames, and a rollover/facial occlusion alert is issued at operation 290.

In exemplary embodiments, tracking of abdominal cavity movement at operation 230 entails analysis of depth data collected for each of a plurality of image frames collected over a monitoring time interval, which may be many hours. Image frames may be collected at some frame rate associated with the 3D camera platform, for example 30, 60, fps, etc. An integrated electronic memory/storage may store compressed image data (e.g., 12-24 hours) with a circular buffer implemented to replace the oldest image data with newest upon reaching memory/storage capacity. All, or a subsampling, of the image frames collected may be processed in substantially real time to determine changes in abdominal cavity position (i.e., changes in depth value) between frames. The abdominal cavity depth/position changes are then tracked over time to compute cavity movement. Cavity position as function of time and/or cavity movement is then compared against one or more predetermined abdominal cavity movement specifications or metrics. If the cavity movement fails to satisfy at least one monitored metric, method 201 proceeds to operation 290 where an alert is issued upon detecting a failure. In some embodiments, failure criteria employed at operation 290 may include facial detection, and/or respiratory rate, and/or respiratory depth or tidal force.

Figure 5A:
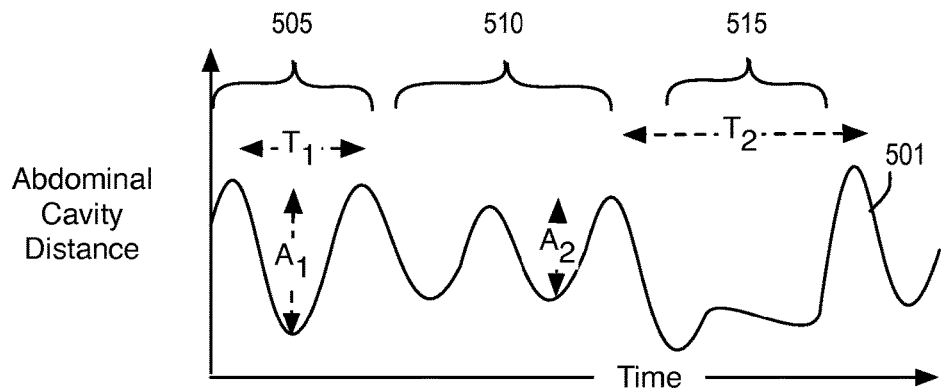
FIG. 5A is a plot of infant abdominal cavity distance over time, in accordance with some embodiments.

In some embodiments, respiratory amplitude is determined based on changes in the distance between the camera baseline and the abdominal cavity surface over time. FIG. 5A is a plot of infant abdominal cavity distance (i.e., depth from 3D camera platform) over time. In the plot illustrated, the solid line 501 represents continuous respiratory data representation that might be derived from depth data sampled at operation 230 (FIG. 2) with a 3D camera having some finite depth resolution and finite depth sampling frame rate. Over a first time interval 505, abdominal cavity distance varies from a maximum distance to a camera baseline at a full exhale state to a minimum distance at a full inhale state (for a camera platform disposed over the infant subject), and back to a maximum distance. This respiratory cycle occurs over respiration period $T_1$ (i.e., respiration rate) and a respiration depth or amplitude $A_1$.

Any known signal processing techniques may be applied to the depth data collected over time to determine rates of change and/or amplitudes of change in depth (abdominal cavity distance) that may then be compared against predetermine thresholds. For example, a difference between a maximum and minimum distances (depths) to the camera baseline may be determined as an indication of respiration depth/tidal volume. In another example, respiratory rate or period is determined based on a difference between image frame timestamps associated with consecutive positions within the respiratory cycle. For example, in the respiratory cycle, there is a static state associated with each of the full exhale (corresponding to the maximum distance to the camera baseline) and with the full inhale (corresponding to the minimum distance to the camera baseline). In the illustrated embodiment, $T_1$ (or the reciprocal respiration rate) is determined by computing a difference between image frame timestamps associated with two consecutive static states where the cavity distance derivative as a function of time is zero.

FIG. 5A further illustrates variation in abdominal cavity displacement cycling over time. If the respiration period $T_1$ is less than a predetermined maximum time threshold (or minimum rate threshold), and respiration amplitude $A_1$ is greater than a predetermined minimum tidal volume threshold, no alert would be issued during time interval 505. During time interval 510, respiration amplitude $A_2$ falls below the minimum tidal volume threshold, and a first alert indicative of shallow breathing is issued by the monitoring system. During time interval 515, at least respiration period $T_2$ falls below the maximum period/minimum rate threshold, and a second alert indicative of apnea is issued by the monitoring system.

In some embodiments, depth values employed in the tracking of abdominal cavity movement in the manner described above are first filtered spatially, temporally, or both. The filtered depth values are then stored to an electronic memory with a timestamp, which may be associated with one or more image frame(s). In some embodiments, determining changes in a depth associated with an abdominal cavity further comprises spatial filtering of depth values. One form of spatial filtering is through masking down a frame-wide depth map to those depth values associated with pixel positions in a region of interest (ROI) within the image frames. In some embodiments, ROI is selected based on a position of a tracked object within the frame, such as one or more facial features.

Figure 5B:
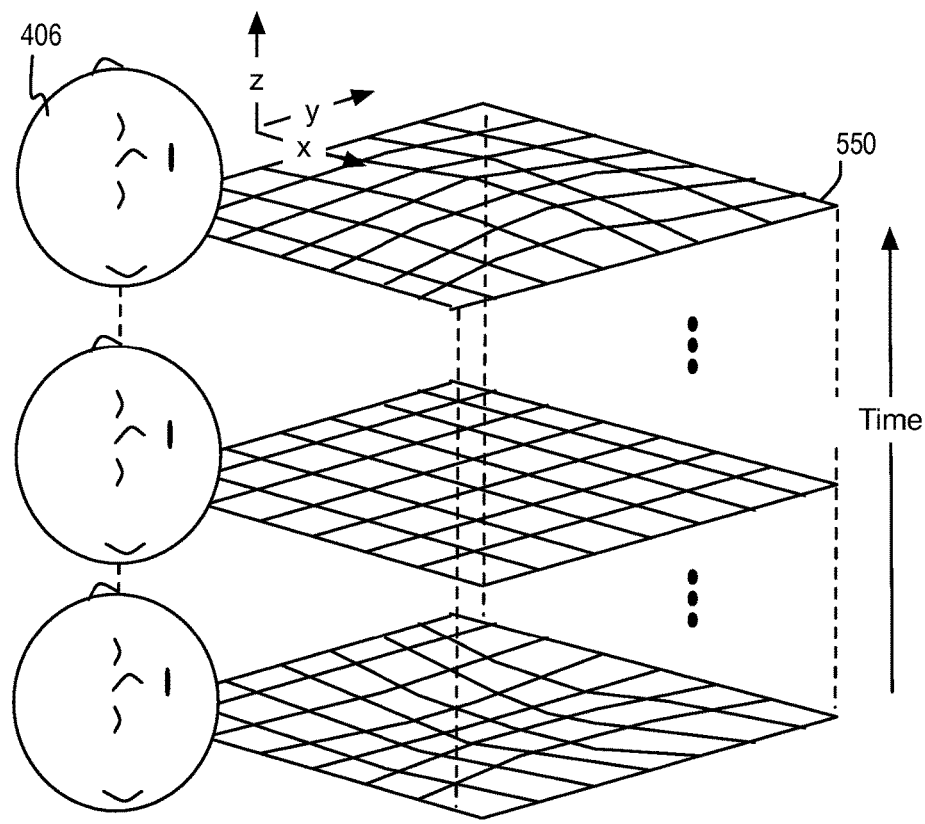
FIG. 5B is a schematic illustrating a region of interest (ROI) over which depth data is filtered and analyzed for changes with time, in accordance with some embodiments.

FIG. 5B is a schematic illustrating a ROI 550 over which depth data is analyzed for changes with time, in accordance with some embodiments. ROI 550 corresponds to a subset of pixels $p_i$ having positions $x_i,y_i$ within a bounding box or window. In some embodiments, ROI 550 is positioned within a frame relative to a location determined for detected infant facial features 406. Once an ROI is selected (or even if no ROI has been selected) depth values may be filtered spatially using any known spatial filtering algorithm in an effort to extract real changes in depth values from measurement noise, for example caused by error in the depth measurement. As one example, a Gaussian filter or other averaging technique may be applied within each image data frame. In some embodiments, a polynomial surface represented by the grid illustrated in FIG. 5B is fit to the 3D spatial coordinates associated with each image data frame. Any multivariate fitting algorithm, such as but not limited to principal component analysis (PCA) may be employed. Depending on the lateral dimensions of the ROI, the polynomial surface fit to the depth data may include higher order curvature terms, or not. For embodiments where the ROI is small, the surface may be assumed linear, and a depth value for a frame modeled as a hyperplane.

In some embodiments, depth values are temporally filtered over a plurality of frames. Any known temporal filtering algorithm may be applied to extract real change in depth values from measurement noise. In some exemplary embodiments, depth values are averaged for a given pixel position $x_i,y_i$ over a plurality of consecutive frames. Noting that the respiration rate of an infant is typically 20-40/minute. Change in depth values associated with abdominal cavity movement may be filtered over window of at least 5 consecutive frames, and as many as 10 consecutive frames without losing significant depth resolution.

In some embodiments, both spatial filtering and temporal filtering are applied to depth values collected over a time interval. In some examples, a set of depth values temporally filtered to arrive at first subset of depth values, which are then spatially filtered to arrive at a second subset of depth values, for example associated with a ROI, which are then analyzed to determined abdominal cavity movement. In some other examples, a set of depth values are spatially filtered to arrive at first subset of depth values, for example associated with a ROI, which are then temporally filtered to arrive at a second subset of depth values, which are then analyzed to determined abdominal cavity movement.

Figure 6:
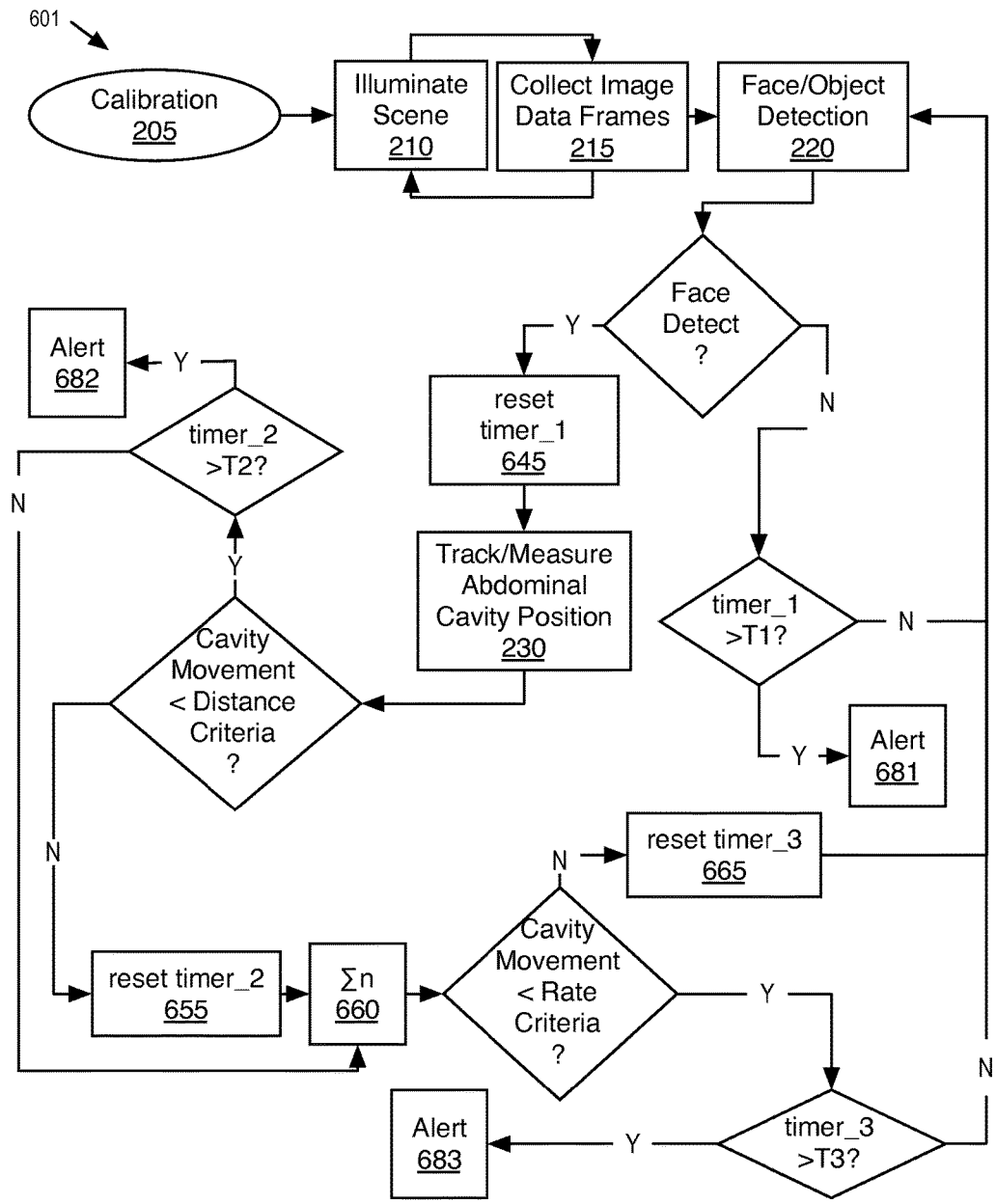
FIG. 6 is a flow diagram of a method for infant monitoring with a 3D camera system, in accordance with some embodiments.

FIG. 6 is a flow diagram of a method 601 for infant monitoring with a 3D camera system, in accordance with some embodiments. Method 601 is one exemplary embodiment of method 201 (FIG. 2), and further illustrates respiratory fault detection. In some embodiments, method 201 is performed by monitoring system 101 (FIG. 1). In exemplary embodiments, method 601 is performed by computer processor(s) integrated into 3D camera platform 120. In other embodiments, at least a portion of method 601 is performed by a computer processor remote from 3D camera platform 120.

Method 601 begins with a system calibration loop performed until the system is initialized. System parameters are set, reset, or bootstrapped, at operation 205. Calibration parameters are updated at operation 205, and the calibration routine continued until calibration criteria are met. In some embodiments, the system is deemed calibrated upon both successful object detection and successful detection of a periodic change in depth values satisfying predetermined respiratory rate and depth thresholds.

Following the calibration phase, method 601 continues to operation 210, where the scene is illuminated, for example with an IR illuminator. At operation 215, image data frames are collected with 3D camera. Operations 210 and 215 continue at a camera frame rate throughout the duration of a runtime phase of method 601. In the exemplary embodiment, image data frames collected at operation 215 are processed through one or more face/object detection algorithms at operation 220. In some embodiments, facial feature detection is performed for a frame as a condition to determining one or more depth values indicative of the abdominal cavity position at operation 230. For example, facial feature position tracking between a current frame and one or more prior frame may be performed at operation 220. In some embodiments, abdominal cavity position is then assessed at operation 230 based on depth values within an ROI in the current frame that has been updated from that of a prior frame based on the facial feature position tracking.

In response to a feature/face detection failure, a flag may be set, and the system waits for successful feature recognition. A time value maintained by first timer is assessed against a time threshold T1, which is a predetermined maximum time for feature recognition to be lost (e.g. 30 seconds). Until the first timer value exceeds time threshold T1, method 601 returns to face/objection detection operation 220 to analyze a subsequent frame. In response to he first timer exceeding time threshold T1, an alert is issued at operation 681. In some embodiments, the alert issued at operation 681 is indicative of infant facial occlusion, for example due to an infant rolling over.

In response to successful facial feature detection, either (or both) of cavity movement depth and rate may be quantified and compared to thresholds. Respiratory cycle depth and rate may parallel criteria assessed independently, with facial recognition dictating whether cavity movement assessment are made. Each of cavity movement depth and cavity movement rate may be assessed using a two-stage "trigger-and-hold" algorithm in which a time to satisfy a predetermined criteria is monitored and an alert issued in response to the criteria not being met within the allotted time. A failure to detect a threshold breathing depth or rate therefore does not induce an alert until the failure state holds for more than a threshold period of time. As infant respiration is may be erratic in the short term, hold time thresholds may advantageously reduce a risk of false alerts. The benefit of minimizing false positives may be balanced with the benefit of rapid detection of a respiratory issue. System sensitivity may be adjusted through the modification of the hold criteria as well as the trigger criteria.

As further illustrated in FIG. 6, in response to successful facial feature detection for the current frame, method 601 proceeds to operation 645 where the first timer time value is reset. At operation 230, abdominal cavity position is tracked, for example through a z-depth measurement as described elsewhere herein. In advantageous embodiments, facial detection operation 220 and abdominal cavity position tracking operation 230 are substantially real time, keeping pace with image data collection operation 215 performed at a camera frame rate. At operation 230, a difference between the abdominal cavity depth (position) for the current frame relative to a reference depth (position) associated with one or more prior frames is determined. In some embodiments, the change in cavity position between the current frame and reference is compared to a minimum cavity movement threshold. In some embodiments, the movement threshold is a portion of a distance between full exhale and full inhale determined during calibration (e.g., 3 mm). A maximum cavity movement threshold may be implemented as well.

In response to failing to meet the cavity movement threshold, a time value maintained by second timer is assessed against a time threshold T2, which is a predetermined maximum time before a next breath must be detected (e.g. 30 seconds). In response to the second timer exceeding time threshold T2, an alert is issued at operation 682. In some embodiments, the alert issued at operation 682 is indicative of respiration depth falling below the threshold.

In response to the meeting the cavity movement threshold, one breath is deemed detected. In some embodiments, in response to the meeting the cavity movement threshold, the current frame is designated the next reference frame from which a threshold cavity movement is to be detected. In this manner method 601 may proceed by detecting respiratory half cycles; repeatedly thresholding the incremental distance between exhale and inhale, and then the distance between inhale and exhale. Method 601 proceeds to operation 655 where the second timer time value is reset. Until the second timer value exceeds time threshold T2, method 601 continues to test the cavity movement rate against a predetermined respiratory rate threshold. In some embodiments, a rate determination is based on a time moving average determined at operation 660. The time moving average may be determined for a plurality of most recent frames corresponding to a time window of 30 seconds. To compute a cavity movement rate, a number of breaths detected over the time moving time window is determined, for example from image frame timestamps, or counted by a timer. The computed rate is then compared against a predetermined rate criteria. The rate criteria may be a band with both upper and lower rate limits, or may be one-side with only and upper limit.

In response to failing the respiration rate criteria over the time window ending with the current frame, a time value maintained by third timer is assessed against a time threshold T3, which is a predetermined maximum time before the rate criteria is met (e.g., 30 seconds). In response to the third timer exceeding time threshold T3, an alert is issued at operation 683. In some embodiments, the alert issued at operation 683 is indicative of respiration rate falling below the threshold. If the third timer has not exceeded time threshold T3, method 601 returns to operation 220 where a next frame is processed. As one example, if a 30 sec moving average of respiration rate dropped below 25 (or went over 60), a countdown period maintained by the third timer would be triggered. Then, if the moving average rate window continued to be out of spec for the time threshold (e.g., 30 sec), the alert threshold is met and an alert issued at operation 683.

In response to satisfying the rate criteria as of the current frame, method 601 proceeds to operation 665 where the third timer time value is reset and method 601 returns to operation 220 where a next frame is processed.

Figure 7:
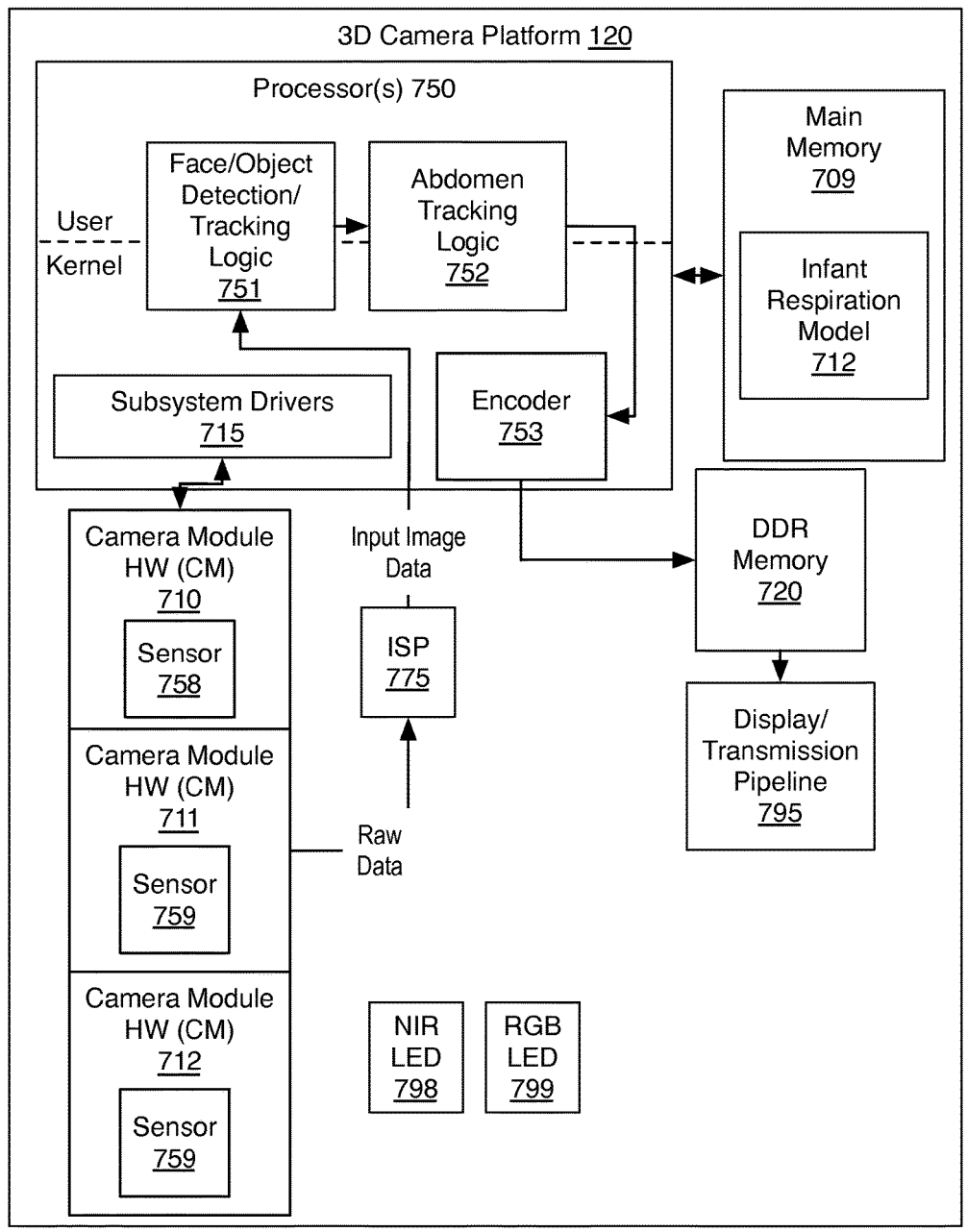
FIG. 7 illustrates a 3D camera platform for infant monitoring, in accordance with some embodiments.

FIG. 7 further illustrates 3D camera platform 120 including, in accordance with some embodiments. FIG. 7 further illustrates how respiratory monitoring components may be integrated with various other components of the 3D camera platform 120. Platform 120 may be an infrastructure device with a grid-based power supply (i.e., plugged-in), or a mobile computing device. A mobile computing device may refer to any device having a processing system and a mobile power source or supply, such as one or more batteries, for example. Examples of a mobile computing device may include a laptop computer, tablet, touch pad, portable computer, handheld computer, palmtop computer, personal digital assistant (PDA), cellular telephone, combination cellular telephone/PDA, television, smart device (e.g., smartphone, tablet or smart television), mobile internet device (MID), messaging device, data communication device, and so forth.

3D camera platform 120 includes hardware CM 710, 711, and 712. In the exemplary embodiment, CM 710 further includes a RGB(NIR) camera sensor 758 while CM 711 and 712 each include a RGB(NIR) camera sensor 759. Sensor 758 may be a HD, FHD, QXGA, WQXGA, QSXGA, or UHD format digital image device, for example. In some embodiments, sensor 758 has at least 8-megapixel resolution. Sensors 759 may be a HD, FHD, QXGA, WQXGA, QSXGA, or UHD format digital image device, for example. In some embodiments, sensors 759 have a lower pixel resolution than sensor 758, for example 1-5 mega pixel. 3D camera platform 120 may therefore generate three image frames concurrently, for example to provide RGB and/or IR image data and image depth data for an input image. In exemplary video embodiments, sensors 758, 759 output multiple consecutively exposed frames of a scene illuminated by an on-board illumination source, such as NIR LED 798 and/or RGB LED 799.

Camera sensors 758, 759 may provide a color resolution of 8 bits, or more, per pixel, and be operable to capture continuous video frames progressively. Sensor 758 may have a pixel frequency of 170 MHz, or more. Sensors 758, 759 may include an RGB Bayer color filter, an analog amplifier, an A/D converter, other components to convert incident light into a digital signal corresponding to raw image data. Sensors 758, 759 may be controlled to operate a rolling shutter or electronic focal plane shutter process where pixels are read out progressively in a line-sequential fashion for a frame. CM 710, 711, and 712 may each output raw data associated with consecutively exposed frames in conformance with any known streaming protocol, such as a MIPI.

In the exemplary embodiment, raw image/video data output by CM 711 and 712 is input to ISP 775. ISP 775 is to receive and analyze frames of raw video data during the horizontal and/or vertical blanking periods associated with CM 710-712. During raw image data processing of RGB image data, ISP 775 may perform one or more of color space conversion, noise reduction, pixel linearization, and shading compensation, for example. In some embodiments, raw image data is passed through ISP 775 to be processed downstream by a programmable microprocessor 750.

Image data output by ISP 775 may be buffered and queued as input image data ready for further image processing, facial detection, and depth difference determinations in accordance with one or more of the embodiments described elsewhere herein. In embodiments, processor(s) 750 includes logic to perform abdominal cavity position tracking and thresholding operations described elsewhere herein. In embodiments, processor(s) 750 includes logic to perform the abdominal cavity movement distance and rate testing described elsewhere herein. In some embodiments, processor(s) 750 includes logic to perform one or more of the operations of method 201 (FIG. 2) and/or method 601 (FIG. 6).

In some embodiments, processor(s) 750 includes face and/or object detection logic 751 to detect an infant's facial features, and abdomen tracking logic 752 to track changes in 3D spatial coordinates for points on an abdominal cavity surface over time. In some embodiments, object detection logic 751 is implemented with programmable circuitry including registers that have been configured through software instruction(s). In some embodiments, processor(s) 750 includes a 3D coordinate filter to filter sampled 3D spatial coordinates, for example over a ROI and/or over multiple frames, for example as described elsewhere here. In some embodiments, 3D coordinate filter logic is implemented with programmable circuitry including registers that have been configured through software instruction(s). In some embodiments, processor(s) 750 includes abdominal cavity movement measurement logic to determine change in cavity surface position over time and to compare that movement to distance and rate thresholds, for example as described elsewhere herein. In some embodiments, abdomen tracking logic 752 is implemented with programmable circuitry including registers that have been configured through software instruction(s).

Both software and hardware implementations may be well suited to implementing infant respiratory monitoring in accordance with embodiments described herein. For hardware implementations, face/object detection and/or tracking logic 751, as well as abdomen tracking logic 752, may be implemented by fixed function logic, for example provided by ISP 775. For software implementations, any known programmable processor, including a core of processor(s) 750, an execution unit of a graphics processor, or any vector processor, may be utilized to implement the face/object detection/tracking logic 751, as well as abdomen tracking logic 752. Processor(s) 750 may be solely responsible for generating a respiratory log from changes in depth values over time determined from input image data received from ISP 775. In one exemplary embodiment, face/object detection and/or tracking logic 751, as well as abdomen tracking logic 752, are invoked through the user space of a software stack instantiated by processor(s) 750. In some embodiments, processor(s) 750 executes face/object detection and/or tracking logic 751, as well as abdomen tracking logic 752, in a kernel space of the software stack. In some embodiments, processor(s) 750 is programmed with instructions stored on a computer readable media to cause the processor to perform one or more infant respiratory monitoring operations, for example as described elsewhere herein.

As further illustrated in FIG. 7, logged respiratory data, and/or alerts, and/or image frames may be output to storage/display/transmission pipeline 795. In one exemplary storage pipeline embodiment, both respiratory data and one or more issued alerts are written to electronic memory 720 (e.g., DDR, etc.) to supplement image frame data encoded into a compressed format by A/V encoder 753. Memory 720 may be separate or a part of a main memory 709 accessible to processor 750. Alternatively, or in addition, storage/display/transmission pipeline 795 is to transmit respiratory data, and/or alerts as metadata associated with compressed video data to receivers remote to camera platform 120.

Figure 8:
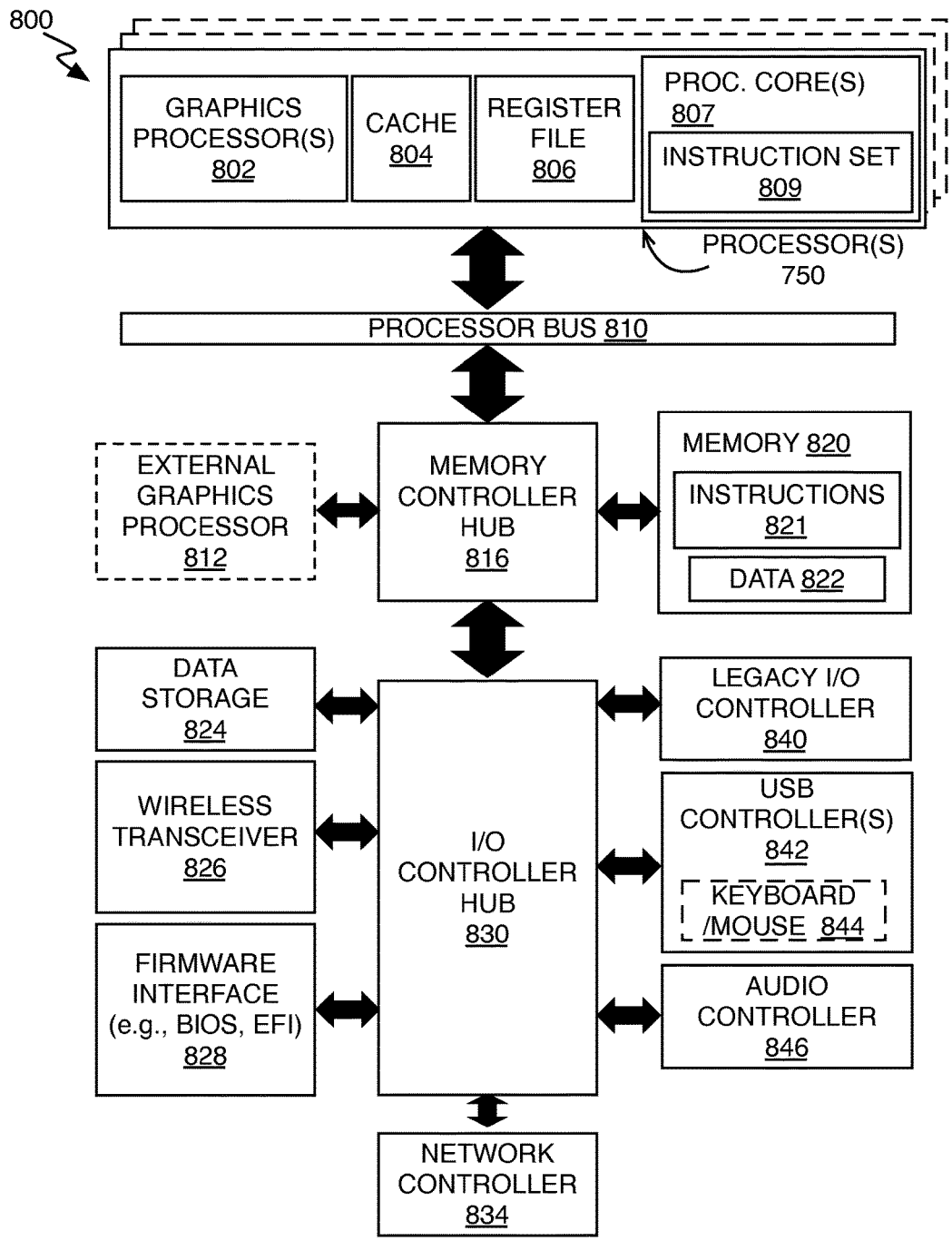
FIG. 8 is a block diagram of a data processing system, according to some embodiments.

FIG. 8 block diagrams a data processing system 800 that may be operated to monitor infant respiration. Data processing system 800 includes one or more processors 750 and one or more graphics processors 801, and may be implemented in a single processor desktop system, a multiprocessor workstation system, or a server system having a large number of processors 850 or processor cores 807. In another embodiment, the data processing system 800 is a system-on-a-chip (SoC) integrated circuit for use in mobile, handheld, or embedded devices.

An embodiment of data processing system 800 can include, or be incorporated within a server-based gaming platform, a game console, including a game and media console, a mobile gaming console, a handheld game console, or an online game console. In some embodiments, data processing system 800 is a mobile phone, smart phone, tablet computing device or mobile Internet device. Data processing system 500 can also include, couple with, or be integrated within a wearable device, such as a smart watch wearable device, smart eyewear device, augmented reality device, or virtual reality device. In some embodiments, data processing system 800 is a television or set top box device having one or more processors 502 and a graphical interface generated by one or more graphics processors 508.

In some embodiments, the one or more processors 802 each include one or more processor cores 807 to process instructions which, when executed, perform operations for system and user software. In some embodiments, each of the one or more processor cores 807 is configured to process a specific instruction set 809. In some embodiments, instruction set 809 may facilitate Complex Instruction Set Computing (CISC), Reduced Instruction Set Computing (RISC), or computing via a Very Long Instruction Word (VLIW). Multiple processor cores 807 may each process a different instruction set 809, which may include instructions to facilitate the emulation of other instruction sets. Processor core 807 may also include other processing devices, such a Digital Signal Processor (DSP).

In some embodiments, the processor 802 includes cache memory 804. Depending on the architecture, the processor 802 can have a single internal cache or multiple levels of internal cache. In some embodiments, the cache memory is shared among various components of the processor 802. In some embodiments, the processor 802 also uses an external cache (e.g., a Level-3 (L3) cache or Last Level Cache (LLC)) (not shown), which may be shared among processor cores 807 using known cache coherency techniques. A register file 806 is additionally included in processor 802 which may include different types of registers for storing different types of data (e.g., integer registers, floating point registers, status registers, and an instruction pointer register). Some registers may be general-purpose registers, while other registers may be specific to the design of the processor 802.

In some embodiments, processor 802 is coupled to a processor bus 810 to transmit data signals between processor 802 and other components in system 800. System 800 has a 'hub' system architecture, including a memory controller hub 816 and an input output (I/O) controller hub 830. Memory controller hub 816 facilitates communication between a memory device and other components of system 800, while I/O Controller Hub (ICH) 830 provides connections to I/O devices via a local I/O bus.

Memory device 820 can be a dynamic random access memory (DRAM) device, a static random access memory (SRAM) device, flash memory device, or some other memory device having suitable performance to serve as process memory. Memory 820 can store data 822 and instructions 821 for use when processor 802 executes a process. Memory controller hub 816 also couples with an optional external graphics processor 812, which may communicate with the one or more graphics processors 808 in processors 802 to perform graphics and media operations.

In some embodiments, ICH 830 enables peripherals to connect to memory 820 and processor 802 via a high-speed I/O bus. The I/O peripherals include an audio controller 846, a firmware interface 828, a wireless transceiver 826 (e.g., Wi-Fi, Bluetooth), a data storage device 824 (e.g., hard disk drive, flash memory, etc.), and a legacy I/O controller for coupling legacy (e.g., Personal System 2 (PS/2)) devices to the system. One or more Universal Serial Bus (USB) controllers 542 connect input devices, such as keyboard and mouse 844 combinations. A network controller 834 may also couple to ICH 830. In some embodiments, a high-performance network controller (not shown) couples to processor bus 810.

Figure 9:
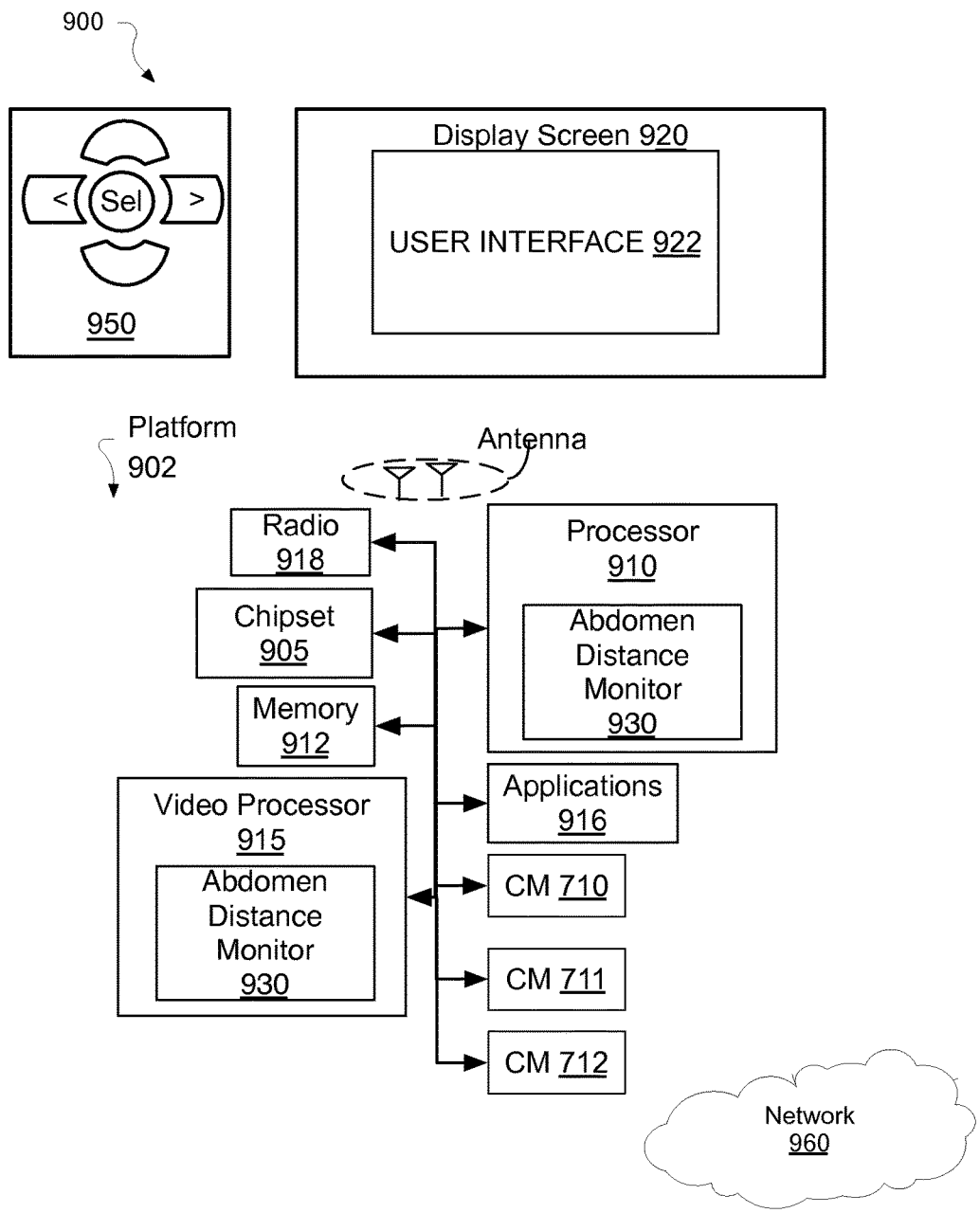
FIG. 9 is a diagram of an exemplary ultra-low power system with a 3D camera-based respiratory monitor, in accordance with some embodiments.

FIG. 9 is a diagram of an exemplary ultra-low power system 900 incorporating an abdomen distance monitor 930, in accordance with one or more embodiment. System 900 may be a mobile device although system 900 is not limited to this context. System 900 may be incorporated into a wearable computing device, laptop computer, tablet, touch pad, handheld computer, palmtop computer, cellular telephone, smart device (e.g., smart phone, smart tablet or mobile television), mobile internet device (MID), messaging device, data communication device, and so forth. System 900 may also be an infrastructure device. For example, system 900 may be incorporated into a large format television, set-top box, security monitor, desktop computer, or other home or commercial network device.

System 900 includes a device platform 902 that may implement all or a subset of the various respiratory monitoring methods and any of the logic blocks/circuitry described above in the context of FIG. 1-8. In various exemplary embodiments, video processor 915 executes at least one of pixel depth sampling, filtering, object tracking, and cavity movement monitoring, for example as described above. Video processor 915 includes logic circuitry 930 implementing respiratory monitoring based on 3D data from an input image, for example as described elsewhere herein. Alternatively, central processor 910 includes logic circuitry 930 implementing respiratory monitoring based on 3D data from an input image, for example as described elsewhere herein. In some embodiments, one or more computer readable media may store instructions, which when executed by CPU 910 and/or video processor 915, cause the processor(s) to execute one or more 3D image data-based respiratory monitoring method, such as any of those described in detail above. A measured respiration rate and/or tidal volume determined from the 3D image data may then be stored in memory 912.

In embodiments, device platform 902 is coupled to a human interface device (HID) 920. Platform 902 may collect raw image data with CM 710, 711, 712, which is processed and output to HID 920. A navigation controller 950 including one or more navigation features may be used to interact with, for example, device platform 902 and/or HID 920. In embodiments, HID 920 may include any television type monitor or display coupled to platform 902 via radio 918 and/or network 960. HID 920 may include, for example, a computer display screen, touch screen display, video monitor, television-like device, and/or a television to receive touch inputs while an input image is displayed on display 922.

In embodiments, device platform 902 may include any combination of CM 910-912, chipset 905, processors 910, 915, memory/storage 912, applications 916, and/or radio 918. Chipset 905 may provide intercommunication among processors 910, 915, memory 912, applications 916, or radio 918.

One or more of processors 910, 915 may be implemented as one or more Complex Instruction Set Computer (CISC) or Reduced Instruction Set Computer (RISC) processors; x86 instruction set compatible processors, multi-core, or any other microprocessor or central processing unit (CPU).

Memory 912 may be implemented as a volatile memory device such as, but not limited to, a Random Access Memory (RAM), Dynamic Random Access Memory (DRAM), or Static RAM (SRAM). Memory 912 may also be implemented as a non-volatile storage device such as, but not limited to flash memory, battery backed-up SDRAM (synchronous DRAM), magnetic memory, phase change memory, and the like.

Radio 918 may include one or more radios capable of transmitting and receiving signals using various suitable wireless communications techniques. Such techniques may involve communications across one or more wireless networks. Example wireless networks include (but are not limited to) wireless local area networks (WLANs), wireless personal area networks (WPANs), wireless metropolitan area network (WMANs), cellular networks, and satellite networks. In communicating across such networks, radio 618 may operate in accordance with one or more applicable standards in any version.

In embodiments, system 900 may be implemented as a wireless system, a wired system, or a combination of both. When implemented as a wireless system, system 900 may include components and interfaces suitable for communicating over a wireless shared media, such as one or more antennas, transmitters, receivers, transceivers, amplifiers, filters, control logic, and so forth. An example of wireless shared media may include portions of a wireless spectrum, such as the RF spectrum and so forth. When implemented as a wired system, system 900 may include components and interfaces suitable for communicating over wired communications media, such as input/output (I/O) adapters, physical connectors to connect the I/O adapter with a corresponding wired communications medium, a network interface card (MC), disc controller, video controller, audio controller, and the like. Examples of wired communications media may include a wire, cable, metal leads, printed circuit board (PCB), backplane, switch fabric, semiconductor material, twisted-pair wire, co-axial cable, fiber optics, and so forth.

The thresholded pixel value matching and associated object processes comporting with exemplary embodiments described herein may be implemented in various hardware architectures, cell designs, or "IP cores."

While certain features set forth herein have been described with reference to embodiments, this description is not intended to be construed in a limiting sense. Hence, various modifications of the implementations described herein, as well as other implementations, which are apparent to persons skilled in the art to which the present disclosure pertains are deemed to be within the spirit and scope of the present disclosure.

The following paragraphs briefly describe some exemplary embodiments:

In one or more first embodiment, a computer implemented method for respiratory monitoring includes processing a sequence of image frames from camera image sensor data collected over a time interval, determining a depth map associated with each of the frames, determining changes in the depth map over the frames, determining a respiratory cycle over the time interval based on the depth map changes, and generating an alert if the frequency or amplitude of the respiratory cycle fails to satisfy one or more predetermined criteria.

In furtherance of the first embodiments, the method further comprises detecting and tracking an object within the frames. Determining changes in the depth map further comprises selecting a region of interest (ROI) within the frames based on a position of the tracked object within the frames, and tracking depth values limited to within the ROI over the frames.

In furtherance of the first embodiments immediately above, detecting and tracking the object further comprises detecting and tracking one or more facial features.

In furtherance of the first embodiments immediately above, the method further comprises generating an alert in response to failing to detect the one or more facial features.

In furtherance of the first embodiments, determining the respiratory cycle over the time interval based on the depth map changes further comprises at least one of spatially filtering depth values for each of the frames, temporally filtering depth values over a plurality of frames, and storing the filtered depth values in association with a timestamp.

In furtherance of the first embodiments immediately above, determining the respiratory cycle over the time interval based on the depth map changes further comprises determining transitions between exhalation and inhalation based on a maximum and minimum of the filtered depth values over time, determining a frequency of the respiratory cycle based on the transitions between exhalation and inhalation, and determining a magnitude of the respiratory cycle based on a difference between consecutive maximum and minimum depth values.

In furtherance of the first embodiments immediately above, analyzing the rate or amplitude of the changes comprises comparing the respiratory frequency against a predetermined minimum respiration rate threshold, and comparing the respiratory magnitude against a predetermined minimum respiration tidal volume threshold.

In furtherance of the first embodiments immediately above, generating the alert further comprises triggering a first alarm locally, or remotely over a communication network, in response to the respiratory frequency failing to satisfy the predetermined minimum respiration rate threshold for a predetermined period of time, and triggering a second alarm locally, or remotely over a communication network, in response to the respiratory depth failing to satisfy the predetermined minimum tidal volume threshold for a predetermined period of time.

In furtherance of the first embodiments, the method further comprises collecting the image frames with at least one of a plurality of digital cameras, a time of flight digital camera, or a structured light illuminator.

In furtherance of the first embodiments immediately above, the method further comprises illuminating, with a near infrared (NIR) source, at least a portion of the field of view associated with the camera image sensor.

In one or more second embodiments, a computerized respiratory monitoring device, comprises an input port to receive a sequence of image frames from camera image sensor data collected over a time interval, and one or more processors coupled to the input port. The processors are to process a sequence of image frames from camera image sensor data collected over a time interval, determine a depth map associated with each of the frames, determine changes in the depth map over the frames, determine a respiratory cycle over the time interval based on the depth map changes, store an indication of the respiratory cycle to an electronic memory, and generate an alert if the frequency or amplitude of the respiratory cycle fails to satisfy one or more predetermined criteria.

In furtherance of the second embodiments, a processor to determine the respiratory cycle is to determine transitions between exhalation and inhalation based on a maximum and minimum of the filtered depth values over time, determine a frequency of the respiratory cycle based on the transitions between exhalation and inhalation, NS determine a magnitude of the respiratory cycle based on a difference between consecutive maximum and minimum depth values.

In furtherance of the second embodiments immediately above, a processor to analyze the rate or amplitude of the changes is to compare the respiratory frequency against a predetermined minimum respiration rate threshold, and compare the respiratory magnitude against a predetermined minimum respiration tidal volume threshold.

In furtherance of the second embodiments, a processor to determine the respiratory cycle is to spatially filter depth values for each of the frames, or temporally filter depth values over a plurality of frames, and store the filtered depth values in association with a timestamp.

In furtherance of the second embodiments, a processor to determine changes in the depth map is to select a region of interest (ROI) within the frames based on a position of the tracked object within the frames, and track depth values limited to within the ROI over the frames.

In furtherance of the second embodiments, the device further comprises at least one of a plurality of digital cameras, a time of flight digital camera, or a structured light illuminator to generate the camera image sensor data.

In one or more third embodiments, a mobile comprises a mount, a support arm attached to the mount, the support arm configured to suspending one or more objects, and the computerized respiratory monitoring device recited in any one of the second embodiments.

In one or more fourth embodiment, one or more computer-readable storage media includes instructions stored thereon, which when executed by a processor, cause the processor to perform a method comprising processing a sequence of image frames from camera image sensor data collected over a time interval, determining a depth map associated with each of the frames, determining changes in the depth map over the frames, determining a respiratory cycle over the time interval based on the depth map changes, and generating an alert if the frequency or amplitude of the respiratory cycle fails to satisfy one or more predetermined criteria.

In furtherance of the fourth embodiments, the media further comprises instructions stored thereon, which when executed by the processor, further cause the processor to perform the method further comprising detecting and tracking an object within the frames, and determining changes in the depth map further comprises selecting a region of interest (ROI) within the frames based on a position of the tracked object within the frames, and tracking depth values limited to within the ROI over the frames.

In furtherance of the fourth embodiments, detecting and tracking the object further comprises detecting and tracking one or more facial features.

In furtherance of the fourth embodiments immediately above, the media further comprises instructions stored thereon, which when executed by the processor, further cause the processor to perform the method further comprising generating an alert in response to failing to detect the one or more facial features.

In furtherance of the fourth embodiments, determining the respiratory cycle over the time interval based on the depth map changes further comprises at least one of spatially filtering depth values for each of the frames, temporally filtering depth values over a plurality of frames, and storing the filtered depth values in association with a timestamp.

In furtherance of the fourth embodiments, the media further comprises instructions stored thereon, which when executed by the processor, further cause the processor to perform the method further comprising spatially filtering depth values for each of the frames, temporally filtering depth values over a plurality of frames, storing the filtered depth values in association with a timestamp, determining transitions between exhalation and inhalation based on a maximum and minimum of the filtered depth values over time, determining a frequency of the respiratory cycle based on the transitions between exhalation and inhalation, and determining a magnitude of the respiratory cycle based on a difference between consecutive maximum and minimum depth values.

In one or more fifth embodiments, a computerized imaging device, comprises a means to perform any one of the first embodiments.

In one or more sixth embodiments, computer-readable storage media includes instructions stored thereon, which when executed by a processor, cause the processor to perform any one of the first embodiments.

In one or more seventh embodiment, a computerized respiratory monitoring device, comprises a means to receive a sequence of image frames from camera image sensor data collected over a time interval, a means to process a sequence of image frames from camera image sensor data collected over a time interval, a means to determine a depth map associated with each of the frames, a means determine changes in the depth map over the frames, a means to determine a respiratory cycle over the time interval based on the depth map changes, a means to store an indication of the respiratory cycle to an electronic memory, and a means to generate an alert if the frequency or amplitude of the respiratory cycle fails to satisfy one or more predetermined criteria.

In furtherance of the seventh embodiment, the device further comprises a means to generate the camera image sensor data.

It will be recognized that the embodiments are not limited to the exemplary embodiments so described, but can be practiced with modification and alteration without departing from the scope of the appended claims. For example, the above embodiments may include specific combination of features. However, the above embodiments are not limited in this regard and, in embodiments, the above embodiments may include undertaking only a subset of such features, undertaking a different order of such features, undertaking a different combination of such features, and/or undertaking additional features than those features explicitly listed. Scope should, therefore, be determined with reference to the appended claims, along with the full scope of equivalents to which such claims are entitled.

What is claimed is:

1. A computerized respiratory monitoring device, comprising:
   an input port to receive a sequence of image frames from camera image sensor data collected over a time interval; and
   one or more processors coupled to the input port, the processors to:
      process a sequence of image frames from camera image sensor data collected over a time interval;
      determine a depth map associated with each of the frames;
      determine changes in the depth map over the frames;
      determine a respiratory cycle over the time interval based on the depth map changes;
      store an indication of the respiratory cycle to an electronic memory; and
      generate an alert if a frequency or an amplitude of the respiratory cycle fails to satisfy one or more predetermined criteria, wherein to determine the respiratory cycle, the processor is to:
         determine transitions between exhalation and inhalation based on a maximum and a minimum of filtered depth values associated with a region of interest (ROI) within the images over time;
         determine a frequency of the respiratory cycle based on the transitions between exhalation and inhalation; and
         determine a magnitude of the respiratory cycle based on a difference between consecutive maximum and minimum filtered depth values.

2. The device of claim 1, wherein the processor is further to:
- compare the respiratory frequency against a predetermined minimum respiration rate threshold; and
- compare the respiratory magnitude against a predetermined minimum respiration tidal volume threshold.

3. The device of claim 1, wherein a processor to determine the respiratory cycle is to:
- spatially filter depth values for each of the frames; or
- temporally filter depth values over a plurality of frames; and
- store the filtered depth values in association with a timestamp.

4. The device of claim 1, wherein:
- a processor to determine changes in the depth map is to:
  - select the ROI within the frames based on a position of facial features detected within the frames, in response to succeeding to detect the facial features; and
  - track depth values limited to within the ROI over the frames; and
- a processor is to generate a second alert in response to failing to detect the facial features subsequent to the indication of the respiratory cycle being stored to an electronic memory.

5. The device of claim 1, further comprising:
- at least one of a plurality of digital cameras, a time of flight digital camera, or a structured light illuminator to generate the camera image sensor data.

6. A mobile monitoring platform, comprising:
- a mount;
- a support arm attached to the mount, the support arm configured to suspending one or more objects; and the computerized respiratory monitoring device recited in claim 1.

7. One or more non-transitory computer-readable storage media, with instructions stored thereon, which when executed by a processor, cause the processor to perform a method comprising: processing a sequence of image frames from camera image sensor data collected over a time interval; determining a depth map associated with each of the frames; determining changes in the depth map over the frames; determining a respiratory cycle over the time interval based on the depth map changes, wherein determining the respiratory cycle further comprises: spatially filtering depth values associated with a region of interest (ROI) for each of the frames; temporally filtering depth values over a plurality of frames; storing the filtered depth values in association with a timestamp, determining transitions between exhalation and inhalation based on a maximum and minimum of the filtered depth values over time; determining a frequency of the respiratory cycle based on the transitions between exhalation and inhalation, and determining a magnitude of the respiratory cycle based on a difference between consecutive maximum and minimum depth values; and generating an alert if the a frequency or an amplitude of the respiratory cycle fails to satisfy one or more predetermined criteria.

8. The media of claim 7,
wherein determining changes in the depth map further comprises:
- selecting the ROI within the frames based on a position of facial features detected within the frames in response to succeeding to detect the facial features; and
- tracking depth values limited to within the ROI over the frames; and wherein the processor is further to generate a second alert in response to failing to detect the facial features subsequent to the indication of the respiratory cycle being stored to an electronic memory.

9. The media of claim 8, wherein the facial features exclude eyes.

10. A computer implemented method for respiratory monitoring, comprising:
- processing a sequence of image frames from camera image sensor data collected over a time interval;
- determining a depth map associated with each of the frames;
- determining changes in the depth map over the frames;
- determining a respiratory cycle over the time interval based on the depth map changes; and
- generating an alert if a frequency or an amplitude of the respiratory cycle fails to satisfy one or more predetermined criteria, wherein determining the respiratory cycle over the time interval based on the depth map changes further comprises:
  - determining transitions between exhalation and inhalation based on a maximum and a minimum of filtered depth values over time;
  - determining a frequency of the respiratory cycle based on the transitions between exhalation and inhalation; and
  - determining a magnitude of the respiratory cycle based on a difference between consecutive maximum and minimum filtered depth values.

11. The method of claim 10,
wherein determining changes in the depth map further comprises:
- selecting the ROI within the frames based on a position of facial features detected within the frames, in response to succeeding to detect the facial features;
- tracking depth values limited to within the ROI over the frames; and the method further comprises generating a second alert in response to failing to detect the facial features subsequent to determining the respiratory cycle.

12. The method of claim 11, wherein the facial features exclude eyes.

13. The method of claim 10, wherein determining the respiratory cycle over the time interval based on the depth map changes further comprises at least one of:
- spatially filtering depth values for each of the frames;
- temporally filtering depth values over a plurality of frames; and
storing the filtered depth values in association with a timestamp.

14. The method of claim 10, wherein generating the alert further comprises:
- comparing the frequency against a predetermined minimum respiration rate threshold; and
- comparing the magnitude against a predetermined minimum respiration tidal volume threshold.

15. The method of claim 14, wherein generating the alert further comprises:
- triggering a first alarm locally, or remotely over a communication network, in response to the frequency failing to satisfy the predetermined minimum respiration rate threshold for a predetermined period of time; and
- triggering a second alarm locally, or remotely over a communication network, in response to the magnitude failing to satisfy the predetermined minimum respiration tidal volume threshold for a predetermined period of time.

16. The method of claim 10, further comprising:
collecting the image frames with at least one of:
- a plurality of digital cameras;
- a time of flight digital camera; or
- a structured light illuminator.

17. The method of claim 16, further comprising illuminating, with a near infrared (NIR) source, at least a portion of a field of view associated with the camera image sensor.

* * * * *